US011154357B2

(12) United States Patent
Wu et al.

(10) Patent No.: US 11,154,357 B2
(45) Date of Patent: Oct. 26, 2021

(54) ELECTRICAL GROUNDING FEATURE FOR IRRIGATION FLUID PATH IN CATHETER ASSEMBLY

(71) Applicant: BIOSENSE WEBSTER (ISRAEL) LTD., Yokneam (IL)

(72) Inventors: Steven W. Wu, San Jose, CA (US); Yitzhak T. Levy, Irvine, CA (US); Alexander Lifshitz, Arcadia, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 535 days.

(21) Appl. No.: 16/014,130

(22) Filed: Jun. 21, 2018

(65) Prior Publication Data
US 2019/0388148 A1    Dec. 26, 2019

(51) Int. Cl.
*A61B 18/16* (2006.01)
*A61B 18/14* (2006.01)
(Continued)

(52) U.S. Cl.
CPC .......... *A61B 18/16* (2013.01); *A61B 18/1492* (2013.01); *A61B 2017/00115* (2013.01);
(Continued)

(58) Field of Classification Search
CPC ................ A61B 18/1492; A61B 18/16; A61B 2017/00115; A61B 2018/00029;
(Continued)

(56) References Cited

U.S. PATENT DOCUMENTS 5,738,096 A   4/1998 Ben-Haim
8,956,353 B2   2/2015 Govari et al.
(Continued)

FOREIGN PATENT DOCUMENTS

| AU | 2014203390 A1 | 1/2015 |
| EP | 2823757 A1 | 1/2015 |
| EP | 3040019 A1 | 7/2016 |

OTHER PUBLICATIONS

International Search Report and Written Opinion dated Nov. 19, 2019 for International Application No. PCT/IB2019/055058, 11 pages.

*Primary Examiner* — Michael F Peffley
*Assistant Examiner* — Amanda L Zink
(74) *Attorney, Agent, or Firm* — Frost Brown Todd LLC

(57) ABSTRACT

An apparatus includes a body, a catheter, and a fluid connector assembly. The catheter extends distally from the body and includes at least one electrode and at least one irrigation port. A fluid conduit is in fluid communication with the at least one irrigation port. A fluid connector assembly extends proximally from the body and includes a fluid connector body and a grounding member. The fluid connector body is configured to couple with a complementary connector associated with a fluid source. A proximal end of the fluid conduit is positioned in an interior region of the fluid connector body. The grounding member is interposed between the proximal end of the fluid conduit and the fluid connector body. The grounding member is in communication with the interior region of the fluid connector body such that the grounding member provides an electrical ground to fluid communicated to the fluid conduit via the fluid connector body.

20 Claims, 4 Drawing Sheets

(51) Int. Cl.
*A61B 17/00* (2006.01)
*A61B 18/00* (2006.01)

(52) U.S. Cl.
CPC ........ *A61B 2018/00029* (2013.01); *A61B 2018/00077* (2013.01); *A61B 2018/00172* (2013.01); *A61B 2018/00178* (2013.01); *A61B 2018/00351* (2013.01); *A61B 2018/00577* (2013.01); *A61B 2018/00642* (2013.01); *A61B 2018/00839* (2013.01); *A61B 2018/00982* (2013.01); *A61B 2018/162* (2013.01); *A61B 2562/0223* (2013.01)

(58) Field of Classification Search
CPC ......... A61B 2018/00077; A61B 2018/00172; A61B 2018/00178; A61B 2018/00351; A61B 2018/00577; A61B 2018/00642; A61B 2018/00839; A61B 2018/0091; A61B 2018/00982; A61B 2018/1472; A61B 2018/162; A61B 2034/2051; A61B 2218/002; A61B 2562/0223; A61B 5/0422; A61B 5/062; A61B 5/6852; A61B 5/7217; A61B 5/743

See application file for complete search history.

(56) References Cited

U.S. PATENT DOCUMENTS

| | | |
|---|---|---|
| 9,801,585 B2 | 10/2017 | Shah et al. |
| 9,907,480 B2 | 3/2018 | Basu et al. |
| 2012/0165735 A1* | 6/2012 | Keh .............. A61M 3/0258 604/151 |
| 2013/0030426 A1* | 1/2013 | Gallardo .......... A61B 18/1492 606/33 |
| 2014/0378902 A1* | 12/2014 | Saba .............. A61B 18/1492 604/151 |
| 2016/0183876 A1* | 6/2016 | Shah .............. A61B 5/7217 600/509 |
| 2017/0319144 A1 | 11/2017 | Shah et al. |
| 2018/0036078 A1 | 2/2018 | Ditter |
| 2018/0056038 A1 | 3/2018 | Aujla |
| 2018/0071017 A1 | 3/2018 | Bar-Tal et al. |

* cited by examiner

ELECTRICAL GROUNDING FEATURE FOR IRRIGATION FLUID PATH IN CATHETER ASSEMBLY

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of energy (e.g., radiofrequency (RF) energy), it may be possible to cease or modify the propagation of unwanted electrical signals from one portion of the heart to another. The ablation process may provide a barrier to unwanted electrical pathways by creating electrically insulative lesions or scar tissue.

In some procedures, a catheter with one or more RF electrodes may be used to provide ablation within the cardiovascular system. The catheter may be inserted into a major vein or artery (e.g., the femoral artery) and then advanced to position the electrodes within the heart or in a cardiovascular structure adjacent to the heart (e.g., the pulmonary vein). The electrodes may be placed in contact with cardiac tissue or other vascular tissue and then activated with RF energy to thereby ablate the contacted tissue. In some cases, the electrodes may be bipolar. In some other cases, a monopolar electrode may be used in conjunction with a ground pad that is in contact with the patient.

Examples of ablation catheters are described in U.S. Pub. No. 2013/0030426, entitled "Integrated Ablation System using Catheter with Multiple Irrigation Lumens," published Jan. 31, 2013, issued as U.S. Pat. No. 10,743,932 on Aug. 18, 2020, the disclosure of which is incorporated by reference herein; U.S. Pub. No. 2018/0071017, entitled "Ablation Catheter with a Flexible Printed Circuit Board," published Mar. 15, 2018, the disclosure of which is incorporated by reference herein; U.S. Pub. No. 2018/0056038, entitled "Catheter with Bipole Electrode Spacer and Related Methods," published Mar. 1, 2018, issued as U.S. Pat. No. 10,702,177 on Jul. 7, 2020, the disclosure of which is incorporated by reference herein; U.S. Pub. No. 2018/0036078, entitled "Catheter with Soft Distal Tip for Mapping and Ablating Tubular Region," published Feb. 8, 2018, issued as U.S. Pat. No. 10,130,422 on Nov. 20, 2018, the disclosure of which is incorporated by reference herein; U.S. Pat. No. 8,956,353, entitled "Electrode Irrigation Using Micro-Jets," issued Feb. 17, 2015, the disclosure of which is incorporated by reference herein; and U.S. Pat. No. 9,801,585, entitled "Electrocardiogram Noise Reduction," issued Oct. 31, 2017, the disclosure of which is incorporated by reference herein.

Some catheter ablation procedures may be performed using electrophysiology (EP) mapping. Such EP mapping may include the use of sensing electrodes on a catheter (e.g., the same catheter that is used to perform the ablation). Such sensing electrodes may monitor electrical signals within the cardiovascular system to pinpoint the location of aberrant conductive tissue sites that are responsible for the arrhythmia. Examples of an EP mapping system are described in U.S. Pat. No. 5,738,096, entitled "Cardiac Electromechanics," issued Apr. 14, 1998, the disclosure of which is incorporated by reference herein. Examples of an EP mapping catheter is described in U.S. Pat. No. 9,907,480, entitled "Catheter Spine Assembly with Closely-Spaced Bipole Microelectrodes," issued Mar. 6, 2018, the disclosure of which is incorporated by reference herein.

In addition to using EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, Calif.

While several ablation catheter systems and methods have been made and used, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

I. Exemplary Ablation System and Method

Figure 1:
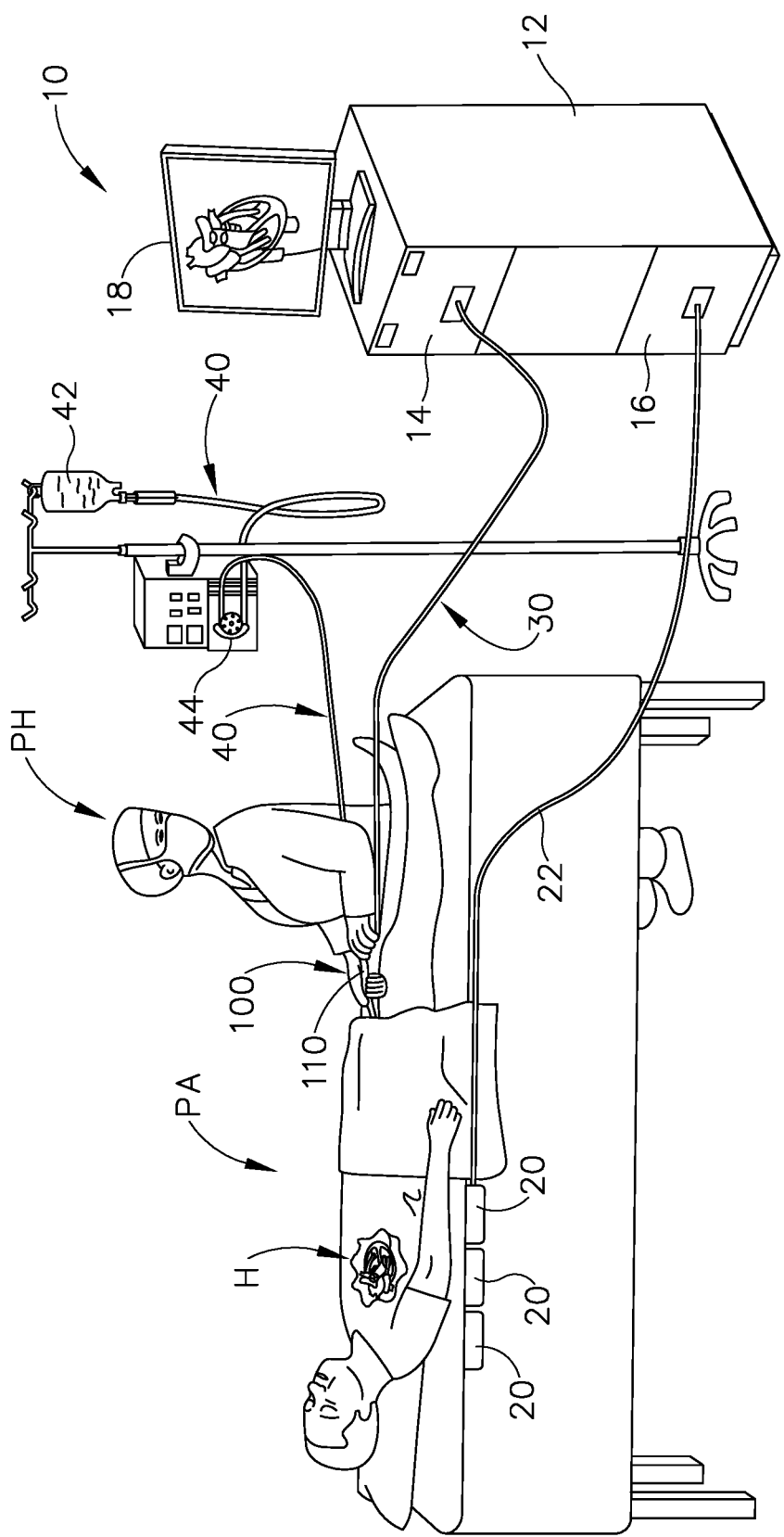
FIG. 1 depicts a schematic view of a medical procedure in which an ablation catheter of an ablation catheter assembly is inserted in a patient.

FIG. 1 shows an exemplary medical procedure and associated components of a cardiac ablation system. In particular, FIG. 1 shows a physician (PH) grasping a handle (110) of an ablation catheter assembly (100), with an ablation catheter (120) (shown in FIG. 2 but not shown in FIG. 1) of ablation catheter assembly (100) disposed in a patient (PA) to ablate tissue in or near the heart (H) of the patient (PA). Ablation catheter assembly (100) is coupled with a guidance and drive system (10) via a cable (30). Ablation catheter assembly (100) is also coupled with a fluid source (42) via a fluid conduit (40). A set of field generators (20) are positioned underneath the patient (PA) and are also coupled with guidance and drive system (10) via a cable (22).

Guidance and drive system (10) of the present example comprises a console (12) and a display (18). Console (12) includes a first driver module (14) and a second driver module (16). First driver module (14) is coupled with ablation catheter assembly (100) via cable (30) and is operable to provide RF power to electrodes (150) of ablation catheter (120) as will be described in greater detail below with reference to FIG. 2. In some versions, first driver module (14) is also operable to receive EP mapping signals from electrodes (150). Console (12) includes a processor (not shown) that processes such EP mapping signals and thereby provides EP mapping as is known in the art. First driver module (14) is also operable to receive position indicative signals from a position sensor (140) (FIG. 2) in ablation catheter (120), as will be described in greater detail below. The processor of console (12) is also operable to process the position indicative signals from position sensor (140) to thereby determine the position of the distal end (122) of ablation catheter (120) within the patient (PA).

Second driver module (16) is coupled with field generators (20) via cable (22). Second driver module (16) is operable to activate field generators (20) to generate an alternating magnetic field around the heart (H) of the patient (PA). For instance, field generators (20) may comprise coils that generate alternating magnetic fields in a predetermined working volume that contains the heart (H).

Display (18) is coupled with the processor of console (12) and is operable to render images of patient anatomy. Such images may be based on a set of preoperatively or intraoperatively obtained images (e.g., a CT or MRI scan, 3-D map, etc.). The views of patient anatomy provided through display (18) may also change dynamically based on signals from position sensor (140). For instance, as distal end (122) of ablation catheter (120) moves within the patient (PA), the corresponding position data from position sensor (140) may cause the processor of console (12) to update the patient anatomy views in display (18) in real time to depict the regions of patient anatomy around distal end (122) as distal end (122) moves within the patient (PA). Moreover, the processor of console (12) may drive display (18) to show locations of aberrant conductive tissue sites, as detected via EP mapping with ablation catheter (120) or as detected via EP mapping with a dedicated mapping catheter (not shown). By way of example only, the processor of console (12) may drive display (18) to superimpose the locations of aberrant conductive tissue sites on the images of the patient's anatomy, such as by superimposing an illuminated dot, a crosshair, or some other form of visual indication of aberrant conductive tissue sites.

The processor of console (12) may also drive display (18) to superimpose the current location of distal end (122) on the images of the patient's anatomy, such as by superimposing an illuminated dot, a crosshair, a graphical representation of distal end (122), or some other form of visual indication. Such a superimposed visual indication may also move within the images of the patient anatomy on display (18) in real time as the physician moves distal end (122) within the patient (PA), thereby providing real-time visual feedback to the operator about the position of distal end (122) within the patient (PA) as distal end (122) moves within the patient (PA). The images provided through display (18) may thus effectively provide a video tracking the position of distal end (122) within a patient (PA), without necessarily having any optical instrumentation (i.e., cameras) viewing distal end (122). In the same view, display (18) may simultaneously visually indicate the locations of aberrant conductive tissue sites detected through the EP mapping as described herein. The physician (PH) may thus view display (18) to observe the real time positioning of distal end (122) in relation to the mapped aberrant conductive tissue sites and in relation to images of the adjacent anatomical structures in the patient (PA).

Fluid source (42) of the present example comprises a bag containing saline or some other suitable irrigation fluid. Conduit (40) comprises a flexible tube that is further coupled with a pump (44). Pump (44) is positioned along conduit (40) between fluid source (42) and ablation catheter assembly (100). In the present example, pump (44) comprises a peristaltic pump that is operable to selectively drive fluid from fluid source (42) to ablation catheter assembly (100). Alternatively, pump (44) may take any other suitable form.

Figure 2:
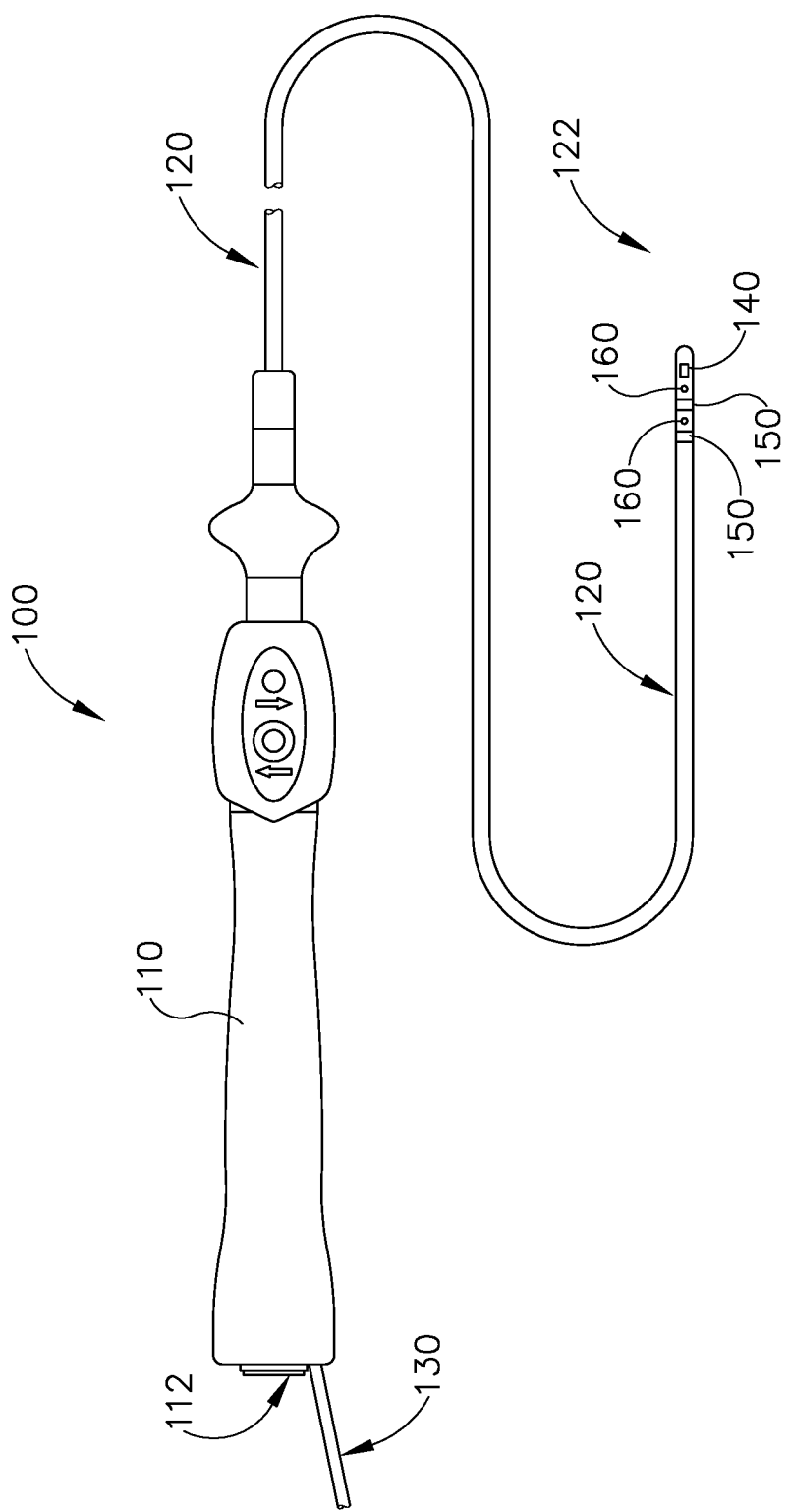
FIG. 2 depicts a top plan view of the ablation catheter assembly of FIG. 1.

FIG. 2 shows ablation catheter assembly (100) in greater detail. As shown, ablation catheter (120) extends distally from handle (110); while a fluid connector assembly (130) extends proximally from handle (110). As also shown in FIG. 2, position sensor (140), electrodes (150), and irrigation ports (160) are located at the distal end (122) of ablation catheter (120). Ablation catheter (120) of the present example is long and flexible and is sized to fit within various lumens and other passageways within the cardiovascular system of the patient (PA).

As noted above, position sensor (140) is operable to generate signals that are indicative of the position and orientation of distal end (122) within the patient (PA). In some versions, position sensor (140) includes a wire coil or a plurality of wire coils (e.g., three coils) that are configured to generate electrical signals in response to the presence of an alternating electromagnetic field; or in response to movement within a static magnetic field. In versions with two or more wire coils forming position sensor (140), the two or more wire coils may be oriented along respective axes that are orthogonal to each other or have any other suitable relationship with each other. In the present example, as noted above, field generators (20) are operable to generate an alternating electromagnetic field, such that sensor (140) generates position indicative signals within the alternating electromagnetic field generated by field generators (20). Other techniques that may be used to generate real-time position data associated with distal end (122) may include wireless triangulation, acoustic tracking, optical tracking, inertial tracking, and the like. Some variations of ablation catheter assembly (100) may lack a position sensor (140).

As also noted above, electrodes (150) may be configured to provide RF ablation or EP mapping functionality. Electrodes (150) may be configured and operable in accordance with the teachings of any of the various patent references that are cited herein. While only two electrodes (150) are shown in FIG. 2, any suitable number of electrodes (150)

may be provided. For instance, several pairs of electrodes (150) may be located at various positions along the length of ablation catheter (120). In some versions, electrodes (150) are configured to provide both RF ablation functionality and EP mapping functionality. In some other versions, electrodes (150) are configured to provide only RF ablation functionality without also providing EP mapping functionality. In still other versions, electrodes (150) are only configured to provide EP mapping functionality without also providing RF ablation functionality. As yet another merely illustrative example, ablation catheter (120) may include some electrodes (150) that are dedicated to providing only RF ablation functionality and other electrodes that are dedicated to providing only EP mapping functionality. Other suitable configurations and functionalities that may be associated with electrodes (150) will be apparent to those skilled in the art in view of the teachings herein.

It may be desirable to provide fluid irrigation at an ablation site. Such irrigation may prevent excessive heating of tissue during the ablation procedure. Moreover, such irrigation may promote electrical conductivity along tissue between electrodes (150). As noted above, distal end (122) of ablation catheter (120) of the present example includes a set of irrigation ports (160), which are in the form of lateral openings on the exterior of ablation catheter (120). While only two irrigation ports (160) are shown in FIG. 2, any suitable number of irrigation ports (160) may be provided. In the example shown in FIG. 2, one irrigation port (160) is longitudinally interposed between electrodes (150) while another irrigation port (160) is distal to electrodes (150). Alternatively, irrigation ports (160) may be located at any other suitable positions on ablation catheter (120).

Figure 3:
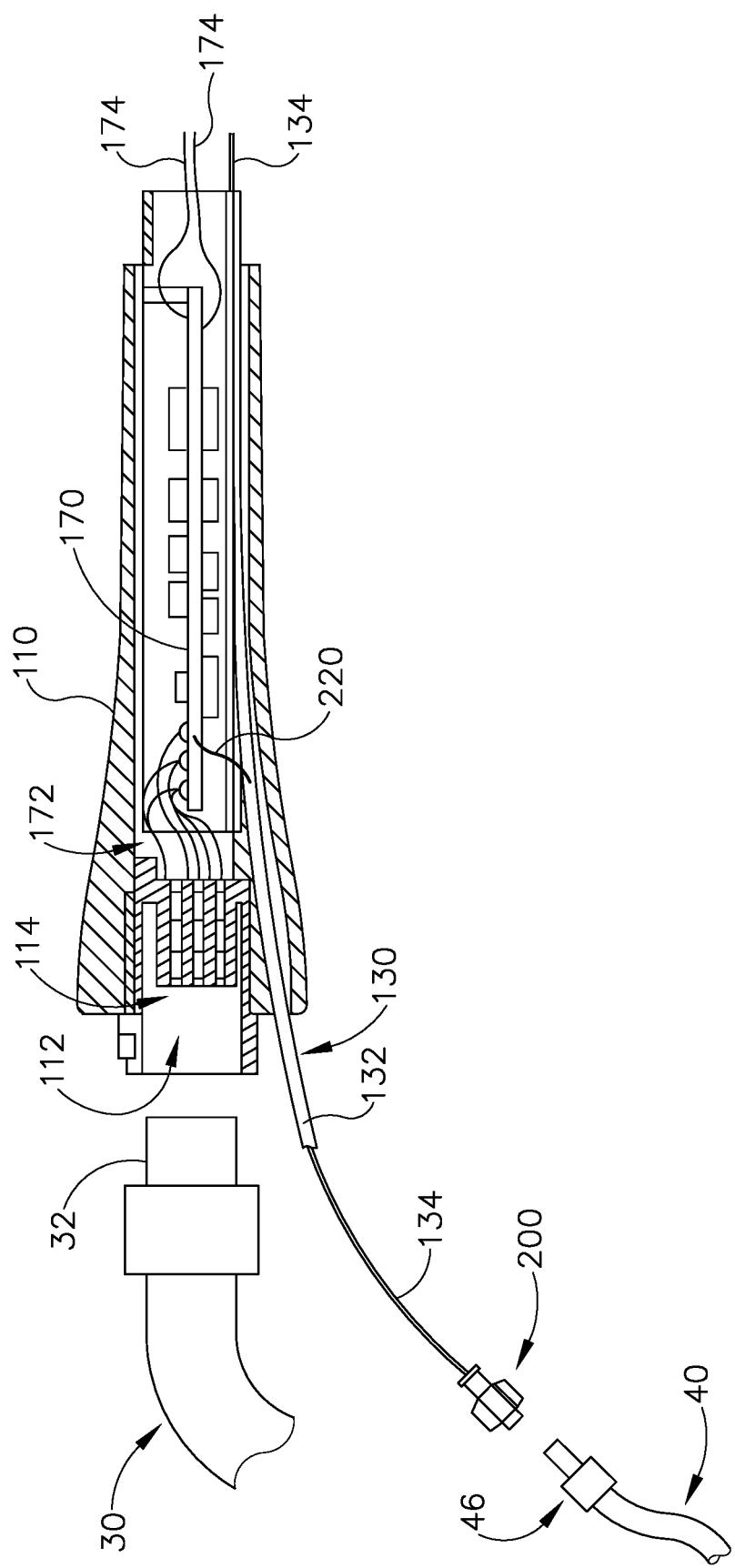
FIG. 3 depicts a cross-sectional side view of a proximal portion of a handle of the ablation catheter assembly of FIG. 2.

Irrigation ports (160) receive irrigation fluid via an irrigation conduit (134) contained in fluid connector assembly (130), which extends proximally from handle (110) as noted above. As shown in FIG. 3, fluid connector assembly (130) is configured to couple with fluid conduit (40). Fluid connector assembly (130) includes an outer sheath (132) and a fluid connector (200). In the present example, outer sheath (132) is electrically insulative. By way of example only, outer sheath (132) may comprise a heat shrink wrap. An irrigation conduit (134) is disposed in outer sheath (132) and is in fluid communication with fluid connector (200). Irrigation conduit (134) comprises a flexible tubular body that extends along the length of ablation catheter (120) and is in fluid communication with irrigation ports (160), thereby providing a path for fluid communication from fluid connector (200) to irrigation ports (160).

Figure 4:
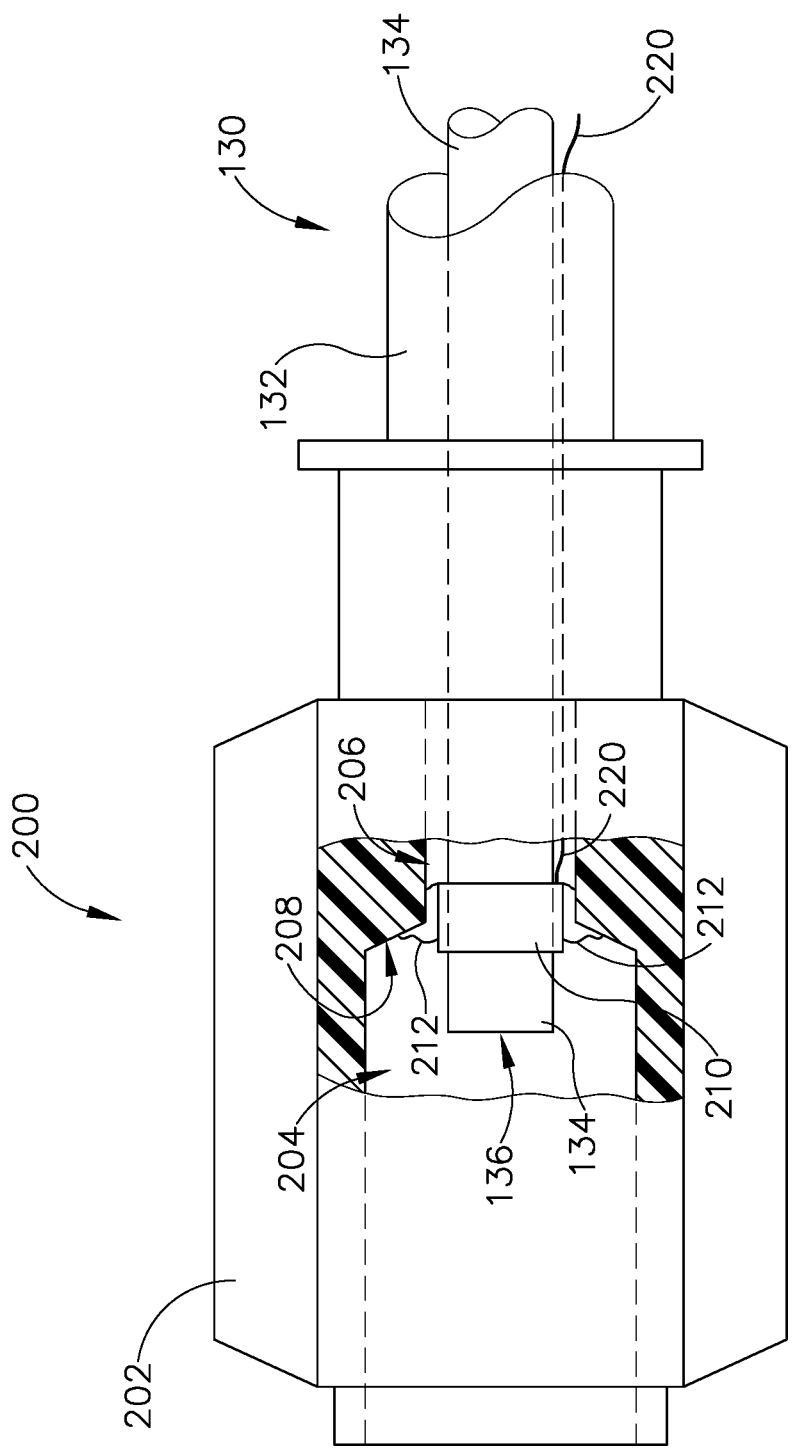
FIG. 4 depicts a top plan view of a fluid connector of the handle of FIG. 3, with a portion of the connector broken away to reveal structures inside the fluid connector.

As shown in FIG. 4, fluid connector (200) of the present example comprises a body (202) defining a first passageway (204) and a second passageway (206), with a tapered transition (208) between passageways (204, 206). In the present example, body (202) is configured as a first luer lock feature that is configured to mate with a second luer lock feature provided by a fluid connector (46) at the distal end of conduit (40). Fluid connectors (46, 200) are thus operable to selectively lock together and thereby provide a path for communication of irrigation fluid from conduit (40) and irrigation conduit (134). Luer lock features are just one merely illustrative example. Other suitable forms that body (202) and fluid connector (46) may take will be apparent to those skilled in the art in view of the teachings herein.

As also shown in FIG. 4, irrigation conduit (134) is positioned within body (202) such that irrigation conduit (134) passes fully through second passageway (206), with the proximal end (136) of irrigation conduit (134) being positioned in first passageway (204). Irrigation conduit (134) is thus in fluid communication with first passageway (204).

As shown in FIG. 3, handle (110) includes a printed circuit board (PCB) (170) with various electrical components that are configured to provide the electrical functionalities described herein. Various suitable components and arrangements that may be incorporated into PCB (170) will be apparent to those skilled in the art in view of the teachings herein. A set of wires (174) extend distally from PCB (170). Wires (174) extend along the length of ablation catheter (120) to position sensor (140) and electrodes (150), thereby providing a path for electrical communication between PCB (170) and position sensor (140); and between PCB (170) and electrodes (150). Another set of wires (172) extend proximally from PCB (170). Wires (172) extend to electrical contacts in an electrical interface (114), which is positioned within a socket (112) at the proximal end of handle (110). As shown in FIG. 3, socket is configured to receive a plug (32) at the distal end of cable (30). Plug (32) includes electrical contacts that mate with the electrical contacts of electrical interface (114) when plug (32) is fully seated in socket (112). These mating contacts thereby provide a path for electrical communication between cable (30) and PCB (170).

II. Exemplary Electrical Grounding of Irrigation Fluid

In some instances, guidance and drive system (10) may tend to pick up a substantial amount of electrical noise in signals from electrodes (150). This may occur when electrodes (150) are used to apply RF ablation, when electrodes (150) are used to provide EP mapping, or when electrodes (150) are used for other purposes (e.g., diagnostic purposes, therapeutic purposes, or other purposes). Such electrical noise may be substantially reduced by providing an electrical ground to the fluid path of irrigation fluid flowing from fluid conduit (40) to irrigation ports (160). However, providing an electrical ground to the fluid path of irrigation fluid flowing from fluid conduit (40) to irrigation ports (160) may tend to present a risk of fluid leaks. Moreover, providing an electrical ground to the fluid path of irrigation fluid flowing from fluid conduit (40) to irrigation ports (160) may tend to present substantial difficulties or expense in manufacturing. It may therefore be desirable to provide an electrical grounding feature for the irrigation fluid while avoiding the risk of fluid leaks; while also avoiding increases in the difficulty or expense of manufacturing. An example of such an electrical grounding feature is described below.

In the present example, ablation catheter assembly (100) includes a conductive cuff (210) and a wire (220) to provide an electrical ground to the irrigation fluid in the fluid path of irrigation fluid flowing from fluid conduit (40) to irrigation ports (160) via irrigation conduit (134). Conductive cuff (210) is formed of an electrically conductive material that is biocompatible and that resists degradation from the presence of irrigation fluid. By way of example only, conductive cuff (210) may be formed of platinum/iridium alloy, palladium/platinum alloy, or any other suitable conductive and biocompatible material(s). Conductive cuff (210) is fixedly and coaxially secured about the exterior of irrigation conduit (134), just distal to proximal end (136). By way of example only, conductive cuff (210) may be fixedly and coaxially secured about the exterior of irrigation conduit (134) via a friction/interference fit or via an adhesive, such as adhesive (212) described below.

Conductive cuff (210) is also fixedly and coaxially secured relative to body (202) via an adhesive (212). By way of example only, adhesive (212) may comprise a biocompatible adhesive or polymer such as polyurethane. In the present example, adhesive (212) is radially interposed between the exterior of conductive cuff (210) and the inner diameter of second passageway (206), thereby providing a fluid tight seal between the exterior of conductive cuff (210) and the inner diameter of second passageway (206). A portion of adhesive (212) is also disposed along tapered transition (208), though this is merely optional. At least some adhesive (212) may also be radially interposed between the exterior of irrigation conduit (134) and the inner diameter of second passageway (206); or between the exterior of irrigation conduit (134) and tapered transition (208). In some instances, adhesive (212) is applied in a succession of layers to minimize the risk of fluid leakage between the exterior of irrigation conduit (134) and the inner diameter of second passageway (206). In the present example, the proximal end of conductive cuff (210) is left exposed by adhesive (212), such that conductive cuff (210) will be in electrical communication with any fluid that is present in first passageway (206) of fluid connector (200).

Wire (220) is secured to conductive cuff (210) and is thereby in electrical communication with conductive cuff (210). By way of example only, wire (220) may be secured to conductive cuff (210) via resistance or laser-based welding. As shown in FIG. 4, wire (220) extends distally from conductive cuff (210), through second passageway (206) alongside irrigation conduit (134). As shown in FIGS. 3-4, wire (220) also extends through fluid connector assembly (130), within outer sheath (132) alongside irrigation conduit (134), eventually exiting outer sheath (132) transversely to reach PCB (170). The distal end of wire (220) is coupled with an electrical ground on PCB (170). The electrical ground on PCB (170) may be coupled with an electrical ground in console (12) via cable (30), such that PCP (170) and cable (30) provide a path for electrically grounding wire (220) to the electrical ground in console (12). PCB (170) may also include resistors, filters, or other components that are configured to provide additional safety and performance characteristics associated with the electrical grounding functionality provided by conductive cuff (210) and wire (220). For example, a diode or an array of diodes (e.g., a transient voltage suppressor, etc.) may be placed in the electrical path to the grounding wire (220) to protect against electrostatic discharge.

While wire (220) is electrically grounded via PCB (170) in the present example, wire (220) may instead be electrically grounded in any other suitable fashion. By way of example only, wire (220) may be directly coupled to a ground path in electrical interface (114) of socket (112), such that wire (220) bypasses PCB (170). Other suitable alternative ground paths for wire (220) will be apparent to those skilled in the art in view of the teachings herein.

In the present example, wire (220) is fluidly isolated from the fluid path of irrigation fluid flowing from fluid conduit (40) to irrigation ports (160), by virtue of adhesive (212). In the present example where the irrigation fluid is saline, which contains electrolytes, the irrigation fluid is capable of conducting electricity. Hence, wire (220) is in electrical communication with irrigation fluid flowing from fluid conduit (40) to irrigation ports (160), by virtue of wire (220) being coupled with conductive cuff (210). Cuff (210) and wire (220) thus cooperate to provide an electrical ground to irrigation fluid flowing from fluid conduit (40) to irrigation ports (160) via irrigation conduit (134).

The above-described configuration and arrangement of conductive cuff (210), wire (220), body (202), and irrigation conduit (134) may provide a substantially robust assembly that is relatively easy and inexpensive to manufacture; and that provides a relatively high degree of reliability. In the event that conductive cuff (210) is somehow decoupled from the exterior of irrigation conduit (134) and from the inner diameter of second passageway (206), conductive cuff (210) will not be able to pass through irrigation conduit (134) and thereby reach irrigation ports (160) since the outer diameter of conductive cuff (210) is greater than the inner diameter of irrigation conduit (134).

When ablation catheter assembly (100) is being used to provide RF ablation, EP mapping, or other electrical functionality, the electrical grounding provided by cuff (210) and wire (220) may provide a safety feature by creating a patient ground that prevents stray electricity from going into the body of the patient (PA). In addition, when ablation catheter assembly (100) is being used to provide EP mapping or other sensing functionality, the electrical grounding provided by cuff (210) and wire (220) may provide performance enhancement by minimizing electrocardiography (ECG) noise in the electrical signals from electrodes (150).

While conductive cuff (210) is positioned within fluid connector (200) in the present example, near the proximal end (136) of irrigation conduit (134), conductive cuff (210) or some other conductive grounding component may instead be placed near distal end (122) of ablation catheter (120). For instance, conductive cuff (210) or some other conductive grounding component may be reduced in size and positioned within the lumen of irrigation conduit (134), near distal end (122) or elsewhere along the length of irrigation conduit (134). In such variations, wire (220) may be repositioned to maintain electrical continuity between conductive cuff (210) (or the variation thereof) and the electrical grounding portion of PCB (170).

Moreover, while conductive cuff (210) is in the form of an annular cuff in the present example, any other suitable configuration may be used to provide an electrical ground to the irrigation fluid flowing from fluid conduit (40) to irrigation ports (160) via irrigation conduit (134). For instance, a grounding member in the form of a conductive rod, conductive stem, conductive strip, or other shape of conductive structure may be radially interposed between the exterior of irrigation conduit (134) and the inner diameter of second passageway (206), with adhesive (212) being used to secure the grounding member in place while also fluidly sealing the rest of the space between the exterior of irrigation conduit (134) and the inner diameter of second passageway (206). Such an alternative grounding member may be oriented parallel with the longitudinal axis shared by irrigation conduit (134) and second passageway (206), while still being laterally offset from the longitudinal axis shared by irrigation conduit (134) and second passageway (206).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a catheter extending distally from the body, wherein at least a portion of the catheter is sized and configured to fit within a lumen of a human cardiovascular system, wherein the catheter includes: (i) a distal end, (ii) a proximal end, (iii) at least one electrode at the distal end, (iv) at least one irrigation port at the distal end, and (v) a fluid conduit in fluid communication with the at least one irrigation port; and (c) a fluid connector assembly extending proximally from the body, wherein the fluid connector assembly comprises: (i) a fluid connector body, wherein the fluid connector body is configured to couple with a complementary connector associated with a fluid source, wherein a proximal end of the fluid conduit is positioned in an interior region of the fluid connector body, and (ii) a grounding member interposed between the proximal end of the fluid conduit and the fluid connector body, wherein the grounding member is in communication (electrically or physically) with the interior region of the fluid connector body such that the grounding member is configured to provide an electrical ground to fluid communicated to the fluid conduit via the fluid connector body.

Example 2

The apparatus of Example 1, wherein the at least one electrode is configured to apply RF energy to tissue.

Example 3

The apparatus of any one or more of Examples 1 through 2, wherein the at least one electrode is configured to pick up signals associated with electrophysiology (EP) mapping within a human cardiovascular system.

Example 4

The apparatus of Example 3, wherein the grounding member is configured to reduce noise in EP mapping signals from the at least one electrode.

Example 5

The apparatus of any one or more of Examples 1 through 4, wherein the grounding member comprises a conductive cuff.

Example 6

The apparatus of Example 5, wherein the conductive cuff is coaxially positioned about the proximal end of the fluid conduit, wherein a portion of the conductive cuff is positioned for exposure to fluid communicated through the fluid conduit.

Example 7

The apparatus of any one or more of Examples 5 through 6, further comprising an adhesive interposed between an exterior of the conductive cuff and an interior portion of the fluid connector body.

Example 8

The apparatus of any one or more of Examples 5 through 7, wherein the conductive cuff comprises platinum/iridium alloy, palladium/platinum alloy, or another highly conductive and biocompatible material.

Example 9

The apparatus of any one or more of Examples 1 through 8, wherein the interior region of the fluid connector body comprises a first portion having a first inner diameter and a second portion having a second inner diameter, wherein the first inner diameter is greater than the second inner diameter, wherein the proximal end of the fluid conduit terminates within the first portion of the interior region, wherein the grounding member is secured to the second portion of the interior region.

Example 10

The apparatus of any one or more of Examples 1 through 9, wherein the body of the apparatus includes an electrical circuit having an electrical ground, wherein the grounding member is electrical communication with the electrical ground of the electrical circuit in the body of the apparatus.

Example 11

The apparatus of Example 10, further comprising a wire extending between the electrical ground of the electrical circuit and the grounding member.

Example 12

The apparatus of Example 11, wherein the wire is fluidly isolated from the interior region of the fluid connector body.

Example 13

The apparatus of any one or more of Examples 10 through 12, further comprising: (a) a cable, wherein the cable is coupled with the body; and (b) a console unit, wherein the cable is further coupled with the console unit, wherein the console unit has an electrical ground, wherein the cable is configured to provide an electrical path between the electrical ground of the electrical circuit in the body and the electrical ground of the console.

Example 14

The apparatus of Example 13, wherein the console unit is further configured to provide RF energy to the at least one electrode via the cable.

Example 15

The apparatus of any one or more of Examples 13 through 14, wherein the console unit is further configured to receive and process EP mapping signals from the at least one electrode via the cable.

Example 16

The apparatus of any one or more of Examples 13 through 14, wherein the catheter further includes a position sensor operable to generate signals indicating a position of the distal end in three-dimensional space, wherein the console is further configured to receive and process the signals from the position sensor.

Example 17

The apparatus of Example 16, further comprising one or more magnetic field generators, wherein the one or more magnetic field generators are configured to generate a magnetic field around at least a portion of a patient, wherein the position sensor is configured to generate signals in response to the generated magnetic field.

Example 18

The apparatus of Example 17, wherein the console is coupled with the one or more magnetic field generators via one or more cables, wherein the console is operable to drive the one or more magnetic field generators to generate the magnetic field.

Example 19

An apparatus comprising: (a) a body; (b) a catheter extending distally from the body, wherein at least a portion of the catheter is sized and configured to fit within a lumen of a human cardiovascular system, wherein the catheter includes: (i) a distal end, (ii) a proximal end, (iii) at least one electrode at the distal end, (iv) at least one irrigation port at the distal end, and (v) a fluid conduit in fluid communication with the at least one irrigation port; and (c) a fluid connector assembly extending proximally from the body, wherein the fluid connector assembly comprises: (i) a fluid connector body, wherein the fluid connector body is configured to couple with a complementary connector associated with a fluid source, wherein a proximal end of the fluid conduit is positioned in an interior region of the fluid connector body, and (ii) a grounding member positioned coaxially about the proximal end of the fluid conduit, wherein the grounding member is in communication with the interior region of the fluid connector body such that the grounding member is configured to provide an electrical ground to fluid communicated to the fluid conduit via the fluid connector body.

Example 20

An apparatus comprising: (a) a body; (b) a catheter extending distally from the body, wherein at least a portion of the catheter is sized and configured to fit within a lumen of a human cardiovascular system, wherein the catheter includes: (i) a distal end, (ii) a proximal end, (iii) at least one electrode at the distal end, (iv) at least one irrigation port at the distal end, and (v) a fluid conduit in fluid communication with the at least one irrigation port; and (c) a fluid connector assembly extending proximally from the body, wherein the fluid connector assembly comprises: (i) a fluid connector body, wherein the fluid connector body is configured to couple with a complementary connector associated with a fluid source, wherein a proximal end of the fluid conduit is positioned in an interior region of the fluid connector body, wherein the proximal end of the fluid conduit and the interior region are coaxially aligned along a common axis, and (ii) a grounding member positioned in the interior region, wherein the grounding member is oriented coaxially with or parallel to the common axis, wherein the grounding member is in communication with the interior region of the fluid connector body such that the grounding member is configured to provide an electrical ground to fluid communicated to the fluid conduit via the fluid connector body.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
(a) a body;
(b) a catheter extending distally from the body, wherein at least a portion of the catheter is sized and configured to fit within a lumen of a human cardiovascular system, wherein the catheter includes:
(i) a distal end,
(ii) a proximal end,
(iii) at least one electrode at the distal end,
(iv) at least one irrigation port at the distal end, and
(v) a fluid conduit in fluid communication with the at least one irrigation port; and
(c) a fluid connector assembly extending proximally from the body, wherein the fluid connector assembly comprises:

(i) a fluid connector body, wherein the fluid connector body is configured to couple with a complementary connector associated with a fluid source, wherein a proximal end of the fluid conduit is positioned in an interior region of the fluid connector body, and (ii) a grounding member interposed between the proximal end of the fluid conduit and the fluid connector body, wherein the grounding member is in communication with the interior region of the fluid connector body such that the grounding member is configured to provide an electrical ground to fluid communicated to the fluid conduit via the fluid connector body.

2. The apparatus of claim 1, wherein the at least one electrode is configured to apply RF energy to tissue.

3. The apparatus of claim 1, wherein the at least one electrode is configured to pick up signals associated with electrophysiology (EP) mapping within a human cardiovascular system.

4. The apparatus of claim 3, wherein the grounding member is configured to reduce noise in EP mapping signals from the at least one electrode.

5. The apparatus of claim 1, wherein the grounding member comprises a conductive cuff.

6. The apparatus of claim 5, wherein the conductive cuff is coaxially positioned about the proximal end of the fluid conduit, wherein a portion of the conductive cuff is positioned for exposure to fluid communicated through the fluid conduit.

7. The apparatus of claim 5, further comprising an adhesive interposed between an exterior of the conductive cuff and an interior portion of the fluid connector body.

8. The apparatus of claim 5, wherein the conductive cuff comprises platinum/iridium alloy, palladium/platinum alloy, or another highly conductive and biocompatible material.

9. The apparatus of claim 1, wherein the interior region of the fluid connector body comprises a first portion having a first inner diameter and a second portion having a second inner diameter, wherein the first inner diameter is greater than the second inner diameter, wherein the proximal end of the fluid conduit terminates within the first portion of the interior region, wherein the grounding member is secured to the second portion of the interior region.

10. The apparatus of claim 1, wherein the body of the apparatus includes an electrical circuit having an electrical ground, wherein the grounding member is electrical communication with the electrical ground of the electrical circuit in the body of the apparatus.

11. The apparatus of claim 10, further comprising a wire extending between the electrical ground of the electrical circuit and the grounding member.

12. The apparatus of claim 11, wherein the wire is fluidly isolated from the interior region of the fluid connector body.

13. The apparatus of claim 10, further comprising:
(a) a cable, wherein the cable is coupled with the body; and
(b) a console unit, wherein the cable is further coupled with the console unit, wherein the console unit has an electrical ground, wherein the cable is configured to provide an electrical path between the electrical ground of the electrical circuit in the body and the electrical ground of the console.

14. The apparatus of claim 13, wherein the console unit is further configured to provide RF energy to the at least one electrode via the cable.

15. The apparatus of claim 13, wherein the console unit is further configured to receive and process EP mapping signals from the at least one electrode via the cable.

16. The apparatus of claim 13, wherein the catheter further includes a position sensor operable to generate signals indicating a position of the distal end in three-dimensional space, wherein the console is further configured to receive and process the signals from the position sensor.

17. The apparatus of claim 16, further comprising one or more magnetic field generators, wherein the one or more magnetic field generators are configured to generate a magnetic field around at least a portion of a patient, wherein the position sensor is configured to generate signals in response to the generated magnetic field.

18. The apparatus of claim 17, wherein the console is coupled with the one or more magnetic field generators via one or more cables, wherein the console is operable to drive the one or more magnetic field generators to generate the magnetic field.

19. An apparatus comprising:
(a) a body;
(b) a catheter extending distally from the body, wherein at least a portion of the catheter is sized and configured to fit within a lumen of a human cardiovascular system, wherein the catheter includes:
   (i) a distal end,
   (ii) a proximal end,
   (iii) at least one electrode at the distal end,
   (iv) at least one irrigation port at the distal end, and
   (v) a fluid conduit in fluid communication with the at least one irrigation port; and
(c) a fluid connector assembly extending proximally from the body, wherein the fluid connector assembly comprises:
   (i) a fluid connector body, wherein the fluid connector body is configured to couple with a complementary connector associated with a fluid source, wherein a proximal end of the fluid conduit is positioned in an interior region of the fluid connector body, and
   (ii) a grounding member positioned coaxially about the proximal end of the fluid conduit, wherein the grounding member is in communication with the interior region of the fluid connector body such that the grounding member is configured to provide an electrical ground to fluid communicated to the fluid conduit via the fluid connector body.

20. An apparatus comprising:
(a) a body;
(b) a catheter extending distally from the body, wherein at least a portion of the catheter is sized and configured to fit within a lumen of a human cardiovascular system, wherein the catheter includes:
   (i) a distal end,
   (ii) a proximal end,
   (iii) at least one electrode at the distal end,
   (iv) at least one irrigation port at the distal end, and
   (v) a fluid conduit in fluid communication with the at least one irrigation port; and
(c) a fluid connector assembly extending proximally from the body, wherein the fluid connector assembly comprises:
   (i) a fluid connector body, wherein the fluid connector body is configured to couple with a complementary connector associated with a fluid source, wherein a proximal end of the fluid conduit is positioned in an interior region of the fluid connector body, wherein the proximal end of the fluid conduit and the interior region are coaxially aligned along a common axis, and (ii) a grounding member positioned in the interior region, wherein the grounding member is oriented coaxially with or parallel to the common axis, wherein the grounding member is in communication with the interior region of the fluid connector body such that the grounding member is configured to provide an electrical ground to fluid communicated to the fluid conduit via the fluid connector body.

* * * * *